United States Patent [19]

Zinnanti, Jr.

[11] Patent Number: 4,580,198

[45] Date of Patent: Apr. 1, 1986

[54] ILLUMINATOR FOR MEDICAL EXAMINATION TELESCOPE

[76] Inventor: Anthony Zinnanti, Jr., 13 Conch La., Canoga Park, Calif. 91307

[21] Appl. No.: 678,064

[22] Filed: Dec. 4, 1984

[51] Int. Cl.⁴ .................. F21L 15/14; A61B 1/06
[52] U.S. Cl. .................... 362/203; 128/23; 362/804
[58] Field of Search .......... 362/32, 202, 203, 804; 128/6, 11, 13, 16, 18, 23

[56] References Cited

U.S. PATENT DOCUMENTS 2,258,074  10/1941  Swanson ........................ 362/203
2,483,665  10/1949  Phillips ......................... 362/203
3,373,737   3/1968  Moore et al. ................. 362/804 X Primary Examiner—Tony M. Argenbright
Attorney, Agent, or Firm—Allen A. Dicke, Jr.

[57] ABSTRACT

The illuminator is especially configured for attachment to examination telescopes. The illuminator has a body which carries a plurality of batteries, a connector at the forward end of the body for detachable attachment onto the illumination nipple on the side of the examination telescope, and a lamp holder which is actuated by the attachment action to complete a circuit through the lamp to provide illumination. The illuminator structure is light and compact so that it can be directly carried on the examination telescope.

16 Claims, 3 Drawing Figures

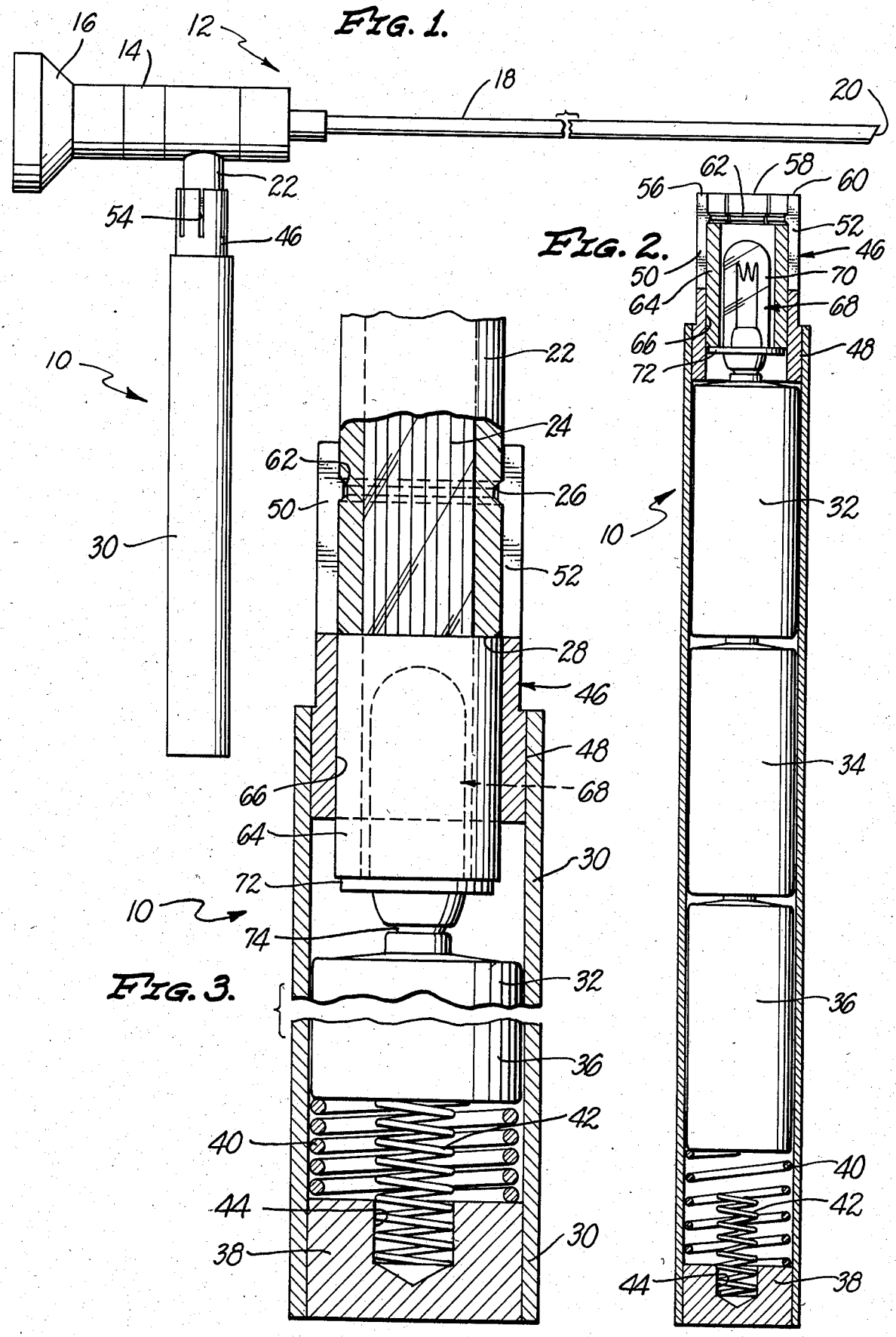

ILLUMINATOR FOR MEDICAL EXAMINATION TELESCOPE

BACKGROUND

This invention is directed to a self-contained illuminator, including battery, switch and lamp for direct attachment to the illumination nipple on an examination telescope to provide the necessary illumination without external electrical or optical connections.

Examination telescopes are well-known and are widely available. Examination telescopes are often employed in visual study of an area which is otherwise inaccessible to view.

Such telescopes are in the form of a long, thin tube with an objective lens at the forward end and an eyepiece at the rear end. Intermediate optics permit the physician to see the view out of the objective lens. Often, the objective lens is prismatic to provide an oblique view off of the axis of the telescope tube.

In order to illuminate the field of view, such telescopes have a fiber optic bundle therein which extends from adjacent the eyepiece to adjacent the objective lens. The optical fibers terminate in a nipple on the side of the telescope adjacent the eyepiece. Illumination supplied to this nipple passes through the fiber optic bundle and illuminates the field of view. Conventionally, the illumination is supplied by a light box set on the floor. A lamp in the light box is supplied by the building power supply. The light from the lamp is cooled and is supplied to a bundle of optical fibers in a cable. This cable terminates in a connector which attaches to the nipple on the side of the telescope. In this way, illumination is provided to the field of view of the telescope. The cumbersome size of the light box and the limited length of the fiber optic supply cable seriously limit the physician in his maneuverability of the telescope. A more independent, flexible and portable system would be helpful to the physician in his use of the telescope.

SUMMARY

In order to aid in the understanding of this invention, it can be stated in essentially summary form that it is directed to an illuminator for an examination telescope. The illuminator has a body which carries at the forward end thereof a connector by which the illuminator can be attached to the light input port of an examination telescope. The body carries a lamp, battery and switch, the switch being actuated to complete a circuit through the battery and lamp when the connector is attached to an examination telescope.

It is, thus, an object and advantage of this invention to provide for examination telescopes an illuminator which is lightweight and portable so that it can be directly attached to the illumination port of the examination telescope and maneuvered with the examination telescope so that the user has both full maneuvering freedom of the telescope and adequate illumination.

It is a further object and advantage of this invention to provide an illuminator for an examination telescope which can be directly attached to the illumination nipple of the examination telescope and is economic of construction so that it can be widely used and is reliable so that it can be employed in medical examination.

Other objects and advantages of this invention will become apparent from a study of the following portion of the specification, the claims and the attached drawings.

BRIEF DESCRIPTION OF THE DRAWINGS

FIG. 1 is a side-elevational view of an examination telescope with the illuminator of this invention attached thereto.

FIG. 2 is an enlarged longitudinal section through the illuminator of this invention.

FIG. 3 is a further enlarged longitudinal section, with parts broken away, showing the examination telescope of this invention attached to the illumination nipple of the examination telescope.

DESCRIPTION OF THE PREFERRED EMBODIMENT

FIGS. 1, 2 and 3 generally indicate the illuminator of this invention at 10. In FIG. 1, it is illustrated in association with a medical examination telescope 12. The telescope 12 includes a housing 14 which carries eyepiece 16 and telescope tube 18. The eyepiece, housing and telescope tube carry optics therein, including an objective lens at tip 20 with the optics arranged so that the view seen in the eyepiece is that view seen by the objective lens at the tip. Telescope tube 18 is sufficiently long and thin to be able to achieve access to restricted areas for the examination thereof.

Quite often, the restricted areas require additional illumination for proper viewing. To achieve illumination of the field of view of the objective lens, in addition to the viewing optics, the telescope tube 18 contains a fiber optic bundle which terminates at tip 20. When lighted, this fiber optic bundle illuminates the field of view. The inner end of the fiber optic bundle terminates in cylindrically tubular nipple 22 which is secured on the side of housing 14. As seen in FIG. 3, the illumination port in the nipple contains optical fibers 24 which, when lighted, illuminate the field of view as previously discussed. Nipple 22 has an annular groove 26 therein and a face 28. This structure is conventional in medical examination telescopes, and such telescopes may be used for examination and inspection in other fields than the medical science.

Illuminator 10 has a right cylindrical tubular body 30 which has an interior diameter sufficient to accept three batteries 32, 34 and 36 in a manner that they are free to axially slide therein. The batteries are cylindrical and are arranged in series; that is, with the same polarity in the same direction. Each battery has a top contact and a bottom contact, each of which is electrically isolated from the cylindrical battery case. Bottom cap 38 is press-fitted into or otherwise secured in the bottom end of body 30. Compression spring 40 engages on the bottom of bottom battery 36. Spring 40 is sufficiently large in diameter to engage upon the crimped case of the battery 36 rather than on the bottom contact interiorly thereof. Spring 40 resiliently holds the series of batteries upward in tubular body 30. Contact spring 42 is engaged in recess 44 in bottom cap 38. The spring is a press-fit into the recess to be held in the recess and is of such length that it does not reach the bottom of battery 36 when the battery is in its upper position shown in FIG. 2. However, when the batteries are forced down in the case against spring 40, they move a sufficient distance that the center contact in the bottom of battery 36 engages on contact spring 42. Thus, the battery contact and spring act as a switch which closes and opens the circuit.

Connector 46 is positioned in the otherwise open upper end of tubular body 30 and is secured in place by press-fit or other suitable means. Connector 46 is generally cylindrically tubular in shape and has a boss 48 which is the part of the connector which enters into tubular body 30 and is sized for that purpose. The forward portion of the connector has a plurality of slots therein, with slots 50 and 52 shown in FIGS. 2 and 3 and slot 54 shown in FIG. 1 There are six such slots to form six fingers. Since FIG. 2 is a central section, the three fingers 56, 58 and 60 are shown in FIG. 2. These slots are sufficiently long in the length of the connector to provide some resiliency to the fingers. The fingers are provided with an annular interior snap ring 62 which is interrupted by the slots which define the fingers. The interior diameter of the connector 46, the length of the slots, and the size of the snap ring 62 are sized so that the connector can attach onto nipple 22 with its snap ring engaging into the annular groove 26 in the nipple. The fingers and snap ring are sized so that the connector can be manually placed onto the nipple and manually removed therefrom by means of resilient deflection of the fingers. In this way, the illuminator 10 is attached to and removed from the nipple of the medical examination telescope.

Lamp holder 64 is a cylindrical tube which slides within the bore 66 of connector 46. Lamp 68 has an envelope 70 which contains the filament of the lamp. The envelope is positioned within the bore of tubular lamp holder 64. At the base of the envelope, lamp 68 has a flange 72 which is one of the contacts of the lamp and which engages on the bottom face of tubular lamp holder 64. The center contact 74 of the lamp extends downward out of the insulator at the base of the lamp. Center contact 74 is in direct contact with the upper, center contact of battery 32. It is that physical engagement that completes the column of batteries, lamp and lamp holder within the housing. When the spring 40 thrusts this column to its upward position shown in FIG. 2, the upward limit is the engagement of the lamp holder 64 on the snap ring 62. Note that in this position, contact spring 42 is not engaged with the bottom of battery 36. When the illuminator is placed on the telescope, nipple 22 enters between the fingers on connector 56 and thrusts the lamp holder 64 downward, as is seen in FIG. 3. When the snap ring 62 is engaged in the corresponding annular groove 46, the interior column of lamp holder, lamp and batteries is thrust downward sufficiently far that the center bottom of battery 36 engages on contact spring 42. Tubular body 30, bottom cap 38, spring 42, connector 46, and lamp holder 64 are all made of metal so that circuit continuity is achieved through the batteries and lamp to light the lamp which provides illumination to the optical fibers 24. In this way, whenever the illuminator is snapped onto the examination telescope, the lamp is lit. No separate switch is required.

The voltage versus light intensity characteristics of the lamp 64 are matched to the voltage available from the batteries so that proper illumination is achieved. Similarly, the rating of the batteries is matched to the life of the lamp at this voltage so that an optimum life is achieved. Of course, the entire instrument, including both the illuminator and the medical examination telescope should be of as light a weight as possible to ease the physician's manipulation of the telescope. The weight of the batteries is also evaluated from this standpoint. In order to minimize the weight of the illuminator, the tubular body, the end cap and the lamp holder are preferably made of lightweight metal such as aluminum. The connector requires greater physical strength and resiliency by reason of its spring fingers. Therefore, the connector is preferably made of stainless steel. The result is a highly portable illuminator which can be snapped onto a medical examination telescope to provide the necessary illumination of the field of view of the telescope.

This invention has been described in its presently contemplated best mode, and it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. An illuminator for an examination telescope having a tubular nipple with an annular groove therearound comprising a light input port thereon:

said illuminator having a body and a connector mounted on said body, said connector being in the form of a cylindrical tube having spring fingers thereon and said spring fingers carry an inwardly facing interrupted snap ring for engagement in an annular groove in the light input port tubular nipple of the examination telescope so that said connector is configured to engage the light input port of the examination telescope;

a lamp holder slidably mounted in said connector tube, a lamp mounted in said lamp holder so that when said illuminator is not mounted on the light input port of the examination telescope, said lamp holder slides forward within said cylindrical connector tube to be retained by said spring fingers and when said illuminator is mounted on the light input port of the examination telescope, said lamp holder is slidably thrust into said connector tube away from said spring fingers by the engagement of said lamp holder on the tubular nipple of the examination telescope and said lamp is positioned to illuminate the light input port;

said body including a battery housing for containing batteries for powering said lamp; and a switch associated with said slidable lamp holder and said lamp so that when there is a battery in said battery housing, said switch provides electrical continuity through the battery and said lamp to light said lamp when said slidable lamp holder is slid away from said inwardly facing snap ring by engagement of said connector on the light input port of an examination telescope.

2. The illuminator of claim 1 wherein said battery housing is the body of said illuminator and said connector is mounted on said body and said lamp is positioned within said connector.

3. The illuminator of claim 1 wherein said lamp is positioned within said slidable lampholder.

4. The illuminator of claim 3 wherein said switch comprises a contact within said battery housing.

5. An illuminator for an examination telescope having a tubular nipple with an annular groove therearound comprising a light input port thereon:

said illuminator having a body and a connector mounted on said body, said connector being in the form of a cylindrical tube having spring fingers thereon and said spring fingers carrying an inwardly facing interrupted snap ring thereon for engagement in the annular groove on the light input port tubular nipple of the examination telescope so that said connector is configured to engage the light input port of the examination telescope so that the illuminator is resiliently attachable and detachable from the examination telescope;

a lamp holder mounted in said body, a lamp mounted in said lamp holder and positioned so when said illuminator is mounted on the light input port of the examination telescope, said lamp holder positions the lamp with respect to the light input port to maintain position of said lamp with the light input port;

said body including a battery housing for containing batteries for powering said lamp; and a switch having a contact within said battery case, connectors connecting said switch, said lamp and a battery in said battery housing in series, said switch being connected to be actuated to light said lamp.

6. The illuminator of claim 5 wherein said battery housing is the body of said illuminator and said connector is mounted on one end of said body and said switch is at the other end of said body.

7. The illuminator of claim 6 wherein said switch comprises a spring mounted on said body for contact with a battery in said body when illumination is desired.

8. The illuminator of claim 7 wherein said lamp is mounted within said connector and when said lamp is moved with respect to said body away from said connector, said lamp thrusts a battery in said housing against said switch spring to close said switch.

9. An illuminator for an examination telescope having a light input port in the form of a nipple having an annular groove therearound, said illuminator comprising:

a tubular body for containing at least one battery;

a connector mounted on said body, said connector having a plurality of spring fingers for engagement on the light input port nipple of an examination telescope, an inwardly directed interrupted snap ring formed on said spring fingers to engage in the annular groove on said nipple when said illuminator is in place on an examination telescope;

a lamp holder slidably positioned in said connector to resiliently slide against said snap ring and having a forward limit position defined by said snap ring, a lamp positioned within said lamp holder for illuminating the light input port when said connector is engaged on the light input port nipple and the lamp holder is engaged by the light input port nipple to thrust said lamp holder back from said snap ring, said lamp being positioned to be engaged by a battery in said body;

a spring in said body for urging a battery in said body toward said lamp to maintain the battery in contact with said lamp; and a switch in said body controlled by said slidable lamp holder for providing continuity through the battery and through said lamp when said lamp holder is thrust away from said snap ring to switch on said lamp.

10. The illuminator of claim 9 wherein a tubular lamp holder is positioned within said connector, said lamp having a flange engaged with said tubular lamp holder to position said lamp with respect to said tubular lamp holder.

11. The illuminator of claim 10 wherein said lamp holder has a front face within said connector and facing toward the open end of said connector and has a rear face facing said body of said illuminator and a battery therein, said flange on said lamp engaging against said rear face of said lamp holder.

12. The illuminator of claim 11 wherein said front face of said lamp holder is positioned for engagement by the nipple of the light input port of the telescope so that said lamp is positioned with respect to the light input port.

13. The illuminator of claim 12 wherein said connector has spring fingers carrying said inwardly directed interrupted snap ring which is for engagement in the annular groove on the nipple of the light input port and said lamp holder engages said snap ring when said illuminator is not mounted on an examination telescope.

14. The illuminator of claim 13 wherein there is a spring in said body engaging said body and a battery in said body to resiliently urge said lamp and said lamp holder toward said snap ring.

15. The illuminator of claim 14 wherein said body has a bottom cap therein and a spring is mounted in said bottom cap, said spring in said bottom cap comprising said switch, the battery in said body engaging said switch spring when said lamp holder is thrust into said body away from said snap ring on said spring fingers.

16. The illuminator of claim 9 wherein said body has a bottom cap therein and a spring is mounted in said bottom cap, said spring in said bottom cap comprising said switch, the battery in said body engaging said switch spring when said lamp holder is thrust into said body by engagement of said spring fingers on a light input port nipple.

* * * * *